US010485452B2

(12) United States Patent
Orellano (10) Patent No.: US 10,485,452 B2
(45) Date of Patent: Nov. 26, 2019

(54) FALL DETECTION SYSTEMS AND METHODS

(71) Applicant: Leonardo Y. Orellano, Tampa, FL (US)

(72) Inventor: Leonardo Y. Orellano, Tampa, FL (US)

(*) Notice: Subject to any disclaimer, the term of this patent is extended or adjusted under 35 U.S.C. 154(b) by 0 days.

(21) Appl. No.: 16/034,266

(22) Filed: Jul. 12, 2018

(65) Prior Publication Data

US 2018/0333083 A1 Nov. 22, 2018

Related U.S. Application Data

(63) Continuation-in-part of application No. 15/050,184, filed on Feb. 22, 2016, now Pat. No. 10,025,908.

(60) Provisional application No. 62/120,784, filed on Feb. 25, 2015, provisional application No. 62/150,253, filed on Apr. 20, 2015.

(51) Int. Cl.
| | |
|---|---|
| *A61B 5/11* | (2006.01) |
| *A61B 5/024* | (2006.01) |
| *G06N 20/00* | (2019.01) |
| *A61B 5/00* | (2006.01) |
| *G16H 40/63* | (2018.01) |
| *G16H 40/67* | (2018.01) |
| *G16H 20/13* | (2018.01) |
| *G06F 15/76* | (2006.01) |

(52) U.S. Cl.
CPC .......... *A61B 5/1117* (2013.01); *A61B 5/0022* (2013.01); *A61B 5/024* (2013.01); *A61B 5/7264* (2013.01); *G06F 15/76* (2013.01); *G06N 20/00* (2019.01); *G16H 20/13* (2018.01); *G16H 40/63* (2018.01); *G16H 40/67* (2018.01); *A61B 2562/0219* (2013.01)

(58) Field of Classification Search
CPC ....... A61B 5/1117; A61B 5/022; A61B 5/024; A61B 5/7264; A61B 2562/0219; G16H 40/67; G16H 40/63; G16H 20/13; G06N 20/00; G06F 15/76
USPC ........................................................ 700/237
See application file for complete search history.

(56) References Cited

U.S. PATENT DOCUMENTS

| | | | | |
|---|---|---|---|---|
| RE39,234 | E | * | 8/2006 | Ostendorf ................. G07F 5/18 221/129 |
| 8,478,493 | B2 | * | 7/2013 | Anderson .............. G05D 1/024 37/348 |
| 9,901,252 | B2 | * | 2/2018 | Tran ..................... G06F 19/3418 |
| 9,901,290 | B2 | * | 2/2018 | Najafi .................... A61B 5/1116 |
| 9,937,305 | B2 | * | 4/2018 | Morrison .......... A61M 15/0001 |
| 10,192,420 | B2 | * | 1/2019 | Boss .................. G08B 21/0446 |
| 10,271,791 | B2 | * | 4/2019 | Donnelly ........... A61B 5/02055 |
| 10,299,691 | B2 | * | 5/2019 | Hughes ................ A61B 5/6832 |
| 2017/0086672 | A1 | * | 3/2017 | Tran ..................... A61B 5/0006 |
| 2017/0347886 | A1 | * | 12/2017 | Tran ..................... G06F 19/3418 |

(Continued)

*Primary Examiner* — Rakesh Kumar
(74) *Attorney, Agent, or Firm* — Stephen E. Zweig (57) ABSTRACT

The present invention relates to systems and methods for fall detection. Specifically, embodiments of the present invention are configured to provide fall detection, including fall prediction and fall prevention, in home health care settings for patients with Alzheimer's disease and related neurodegenerative conditions. In addition, embodiments of the present invention provide continuous fall prediction and detection, including alerts to caregivers, while allowing the patient the flexibility to move outside their home.

1 Claim, 5 Drawing Sheets

(56) References Cited

U.S. PATENT DOCUMENTS

| | | | |
|---|---|---|---|
| 2018/0049926 A1* | 2/2018 | Lin Charna | H04B 1/3888 |
| 2018/0125363 A1* | 5/2018 | Kaib | A61B 5/0022 |
| 2018/0132744 A1* | 5/2018 | Yu | A61B 5/04017 |
| 2018/0150612 A1* | 5/2018 | Konno | A61B 5/046 |
| 2018/0177451 A1* | 6/2018 | Sahin | A61B 5/16 |
| 2018/0184907 A1* | 7/2018 | Tran | G06F 19/3418 |
| 2018/0199884 A1* | 7/2018 | Huppert | A61B 5/6833 |
| 2018/0207373 A1* | 7/2018 | Morrison | A61M 15/0001 |
| 2018/0243611 A1* | 8/2018 | Bradley | A63B 24/0087 |
| 2018/0249963 A1* | 9/2018 | Meyer | A61N 1/371 |
| 2018/0254096 A1* | 9/2018 | Karunanithi | A61B 5/746 |
| 2018/0263534 A1* | 9/2018 | Lee | A61B 5/0022 |
| 2018/0279881 A1* | 10/2018 | McCalmont | A61B 5/747 |
| 2018/0343636 A1* | 11/2018 | Goldstein | G06F 19/00 |
| 2019/0014984 A1* | 1/2019 | Kaib | A61B 5/0022 |
| 2019/0029569 A1* | 1/2019 | Stone | A61B 5/004 |
| 2019/0037299 A1* | 1/2019 | Boesen | H04R 1/1041 |
| 2019/0038133 A1* | 2/2019 | Tran | G06F 19/3418 |
| 2019/0043622 A1* | 2/2019 | Ramaci | G06F 16/90332 |
| 2019/0057593 A1* | 2/2019 | Park | G08B 21/18 |
| 2019/0090781 A1* | 3/2019 | Selvaraj | A61B 5/11 |
| 2019/0099113 A1* | 4/2019 | Roder | G16H 50/20 |
| 2019/0099114 A1* | 4/2019 | Mouradian | A61B 5/1117 |
| 2019/0103007 A1* | 4/2019 | Tan | A61B 5/002 |
| 2019/0116337 A1* | 4/2019 | Naidoo | H04N 7/14 |
| 2019/0133486 A1* | 5/2019 | Felix | A61B 5/04325 |
| 2019/0140911 A1* | 5/2019 | Jain | H04L 41/145 |
| 2019/0159677 A1* | 5/2019 | Soyao | A61B 5/0022 |
| 2019/0171428 A1* | 6/2019 | Patton | G06F 8/60 |
| 2019/0179297 A1* | 6/2019 | Kuroda | G05B 23/0254 |
| 2019/0184184 A1* | 6/2019 | Skelton | A61B 5/103 |
| 2019/0190862 A1* | 6/2019 | Choudhary | G06F 16/24578 |
| 2019/0192052 A1* | 6/2019 | Weffers-Albu | A61B 5/1117 |
| 2019/0200926 A1* | 7/2019 | Donnelly | A61B 5/6804 |
| 2019/0200935 A1* | 7/2019 | Bandyopadhyay | A61B 5/7264 |
| 2019/0206538 A1* | 7/2019 | Xing | G10L 15/18 |

* cited by examiner

FALL DETECTION SYSTEMS AND METHODS

CROSS-REFERENCE TO RELATED APPLICATIONS

This application is a continuation in part of U.S. patent application Ser. No. 15/050,184, filed Feb. 22, 2016; application Ser. No. 15/050,184 claimed the priority benefit of U.S. provisional patent applications 62/150,253, filed Apr. 20, 2015, and 62/120,784, filed Feb. 25, 2015; the entire contents of U.S. patent application Ser. No. 15/050,184, U.S. provisional patent application 62/150,253, and U.S. provisional patent application 62/120,784 are incorporated herein by reference.

BACKGROUND OF THE INVENTION

The present invention relates to fall detection in general, and more particularly, to automatic patient fall detection and prediction in a home health care setting for support of medical treatment of patients having Alzheimer's disease or a related neurodegenerative condition.

Many injuries and even deaths are caused by persons accidentally falling in or near their homes, and such events can be more likely for elderly patients receiving medical treatment in home health care settings, due to cognitive and motor impairments related to their condition, and, in addition, due to side-effects and interaction of medications that may affect the patient's balance or coordination. Fall prediction and detection systems and methods exist, however the protection offered by these systems may be limited to the area of the patient's home, may not provide continuous fall detection, and may be limited to fall detection rather than providing fall prevention. In the earlier and less severe stages of Alzheimer's disease and related neurodegenerative conditions, patients may desire more mobility, and may want to be mobile throughout their neighborhood, however a fall detection system limited in range to the patient's home will not allow the patient the freedom to walk outside their home and move freely around their neighborhood while enjoying the benefit of continuous fall detection.

Some patients at varying stages of neurodegenerative disease may be undergoing medical treatment for their condition in a home health care setting, with the assistance of caregivers aided by a medication hub, an embodiment of the invention disclosed in U.S. Provisional Patent Application Ser. No. 62120784, Medication Adherence Systems and Methods, filed Feb. 25, 2015, which medication hub dispenses medication, provides medication adherence support, and performs dose compliance and dose auditing, supporting the delivery of multiple medications on variable schedules, while monitoring for and preventing adverse drug interactions.

Drug interactions and changes in dosing regimens can affect a patient's balance and potentially degrade a patient's ability to avoid falls.

In view of the foregoing, there is a need in the art of home health care for improved fall prediction and detection systems and methods which: provide increased freedom of mobility to the patient and allow the patient to travel outside their home while enjoying continued fall detection; and, provide improved fall prevention by integrating fall prediction with medication adherence.

BRIEF SUMMARY OF THE INVENTION

The present invention provides improved mobility to patients being monitored for fall detection by integrating the communication facilities of a smart phone with a patient-worn fall detection sensor and the communication and auditing facilities of the medication hub of U.S. Provisional Patent Application Ser. No. 62120784, Medication Adherence Systems and Methods, filed Feb. 25, 2015. As previously discussed, the entire contents of U.S. patent application Ser. No. 15/050,184, U.S. provisional patent application 62/150,253, and U.S. provisional patent application 62/120,784 are incorporated herein by reference.

In addition, the present invention provides improved fall prevention by integrating fall prediction with medication adherence, to continuously assess the possible impact of dose adherence and dosing regimen changes to the patient's balance, and alert caregivers of an increased chance of falling, or adjust dosing to help prevent falls, in addition to detecting falls and alerting caregivers when fall events are detected.

BRIEF DESCRIPTION OF THE DRAWINGS

The above and other features, advantages, and further embodiments of the invention will become more apparent by describing in detail exemplary embodiments thereof with reference to the drawings listed below.

DETAILED DESCRIPTION OF THE INVENTION

Figure 1:
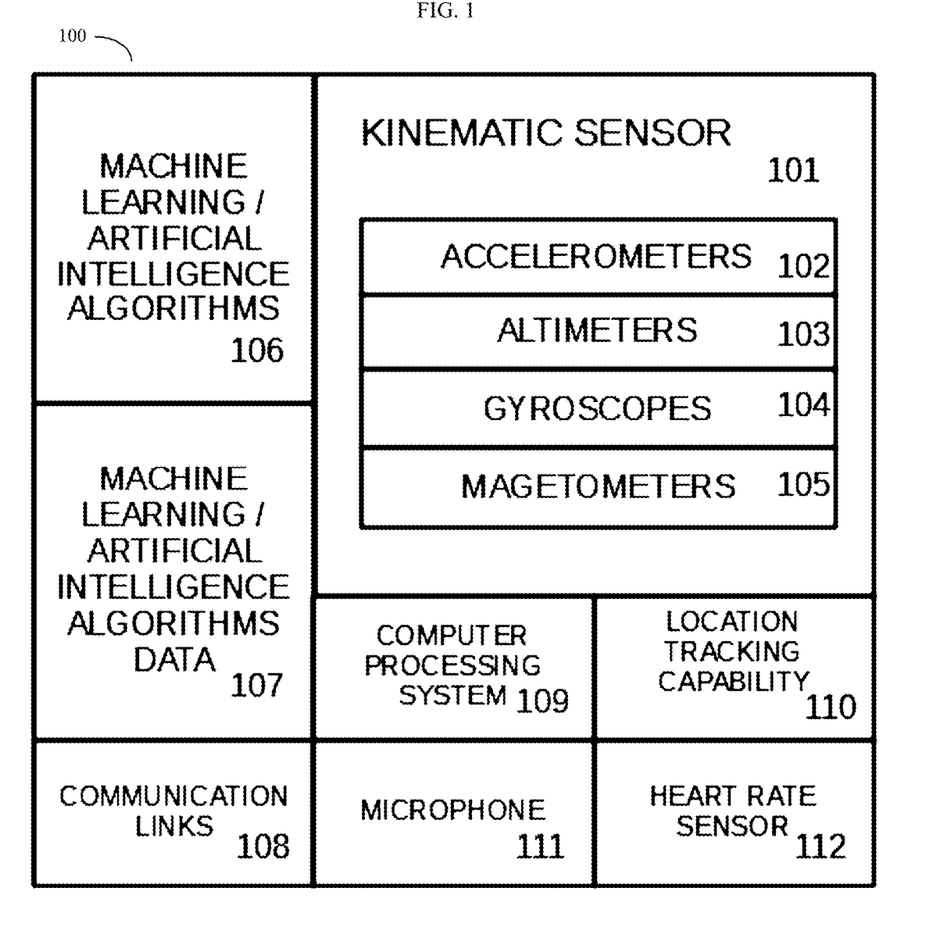
FIG. 1 illustrates a patient-wearable sensor apparatus, in accordance with an embodiment of the present invention.
Figure 2:
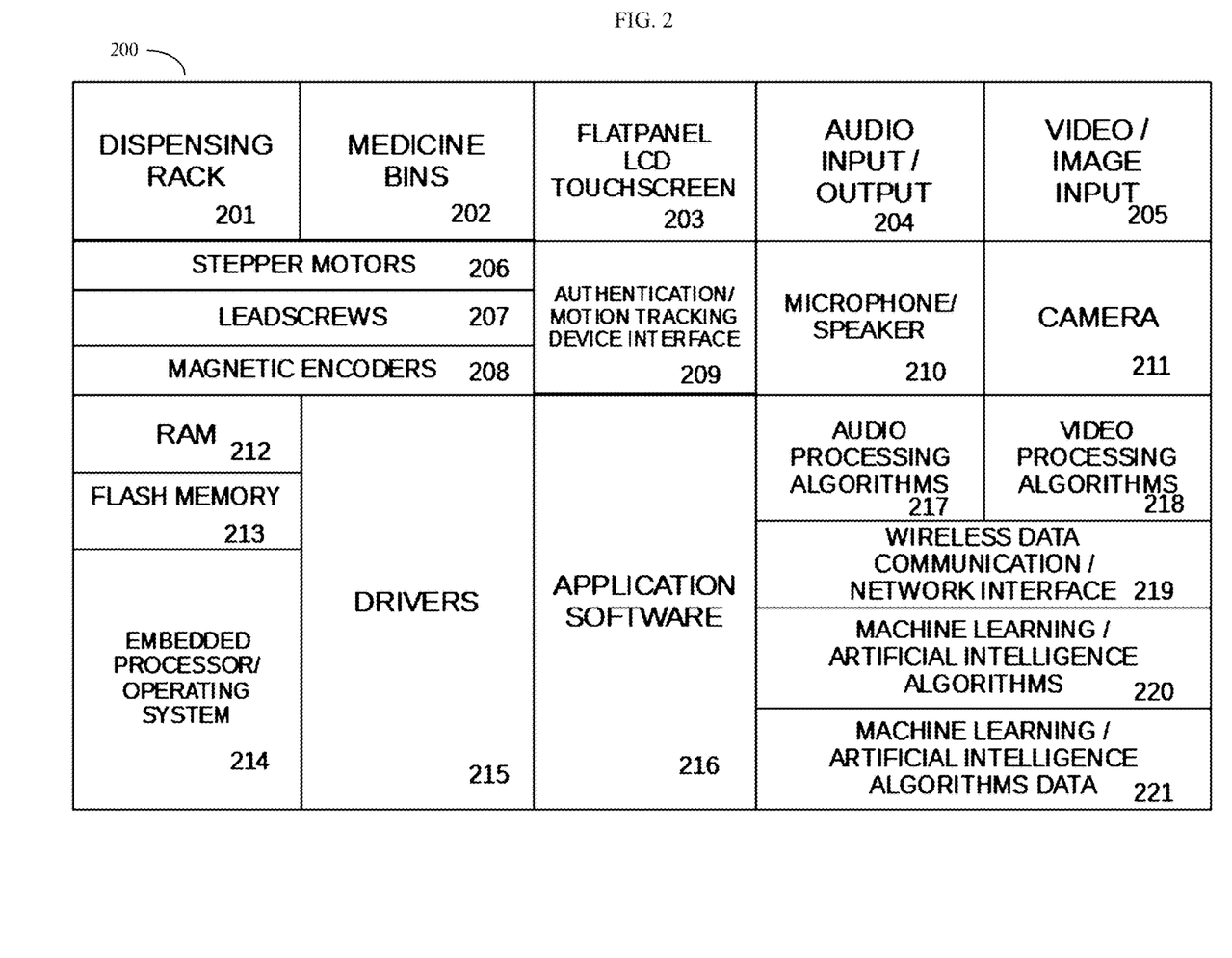
FIG. 2 illustrates a medication hub having one or more machine learning or artificial intelligence algorithm and associated data, in accordance with an embodiment of the present invention.
Figure 3:
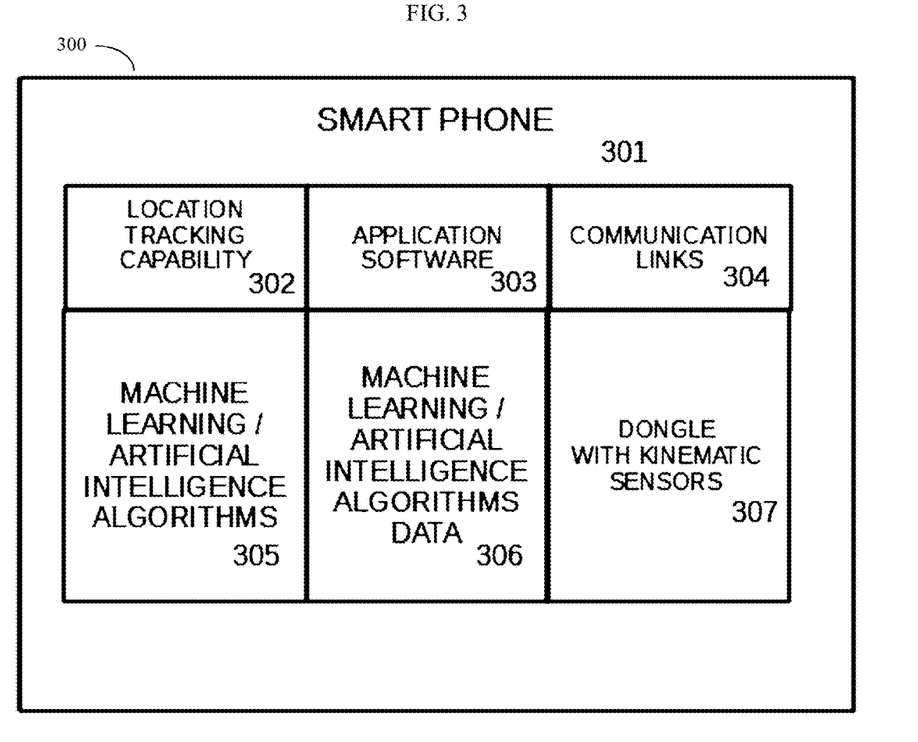
FIG. 3 illustrates a mobile event reporting system, in accordance with an embodiment of the present invention.

An embodiment system of the present invention comprises: a patient-wearable sensor apparatus 100, a mobile event reporting system 300, and a medication hub 200 of an embodiment system of the invention disclosed in U.S. Provisional Patent Application Ser. No. 62120784, Medication Adherence Systems and Methods, filed Feb. 25, 2015, with the additional element, illustrated in FIG. 2, of one or more machine learning or artificial intelligence algorithm 220 and associated data 221, in the medication hub 200 of embodiments of the present invention.

A patient-wearable sensor apparatus 100 illustrated in FIG. 1, of embodiments of the present invention is equipped with: kinematic sensor 101, said kinematic sensor measuring and reporting kinematic data representative of patient acceleration, orientation, angular momentum, and altitude, and said kinematic sensor including: one or more of an accelerometer 102 measuring acceleration, an altimeter 103 measuring altitude, a gyroscope 104 measuring angular momentum, and a magnetometer 105 measuring orientation; one or more of a machine learning or artificial intelligence algorithm 106 and associated data 107, where said associated data 107 may include training data, test data, validation data, historical data, alert thresholds, fall prediction thresholds, or profile data, and said one or more machine learning or artificial intelligence algorithm 106 may include: a neural network, a support vector machine, a decision tree, a classification tree, a regression tree, a random forest, a Bayes classifier, a genetic algorithm, or any other machine learning or artificial intelligence algorithm known to one of ordinary skill in the art; communication links 108, including one or more of Wifi, Zigbee, Bluetooth, ANT, ANT+, Broadband wireless, cellular communication, or other communication links known to one of ordinary skill in the art; and, a computer processing system 109, including one or more processor, associated memory, operating system, and application software. In some embodiments,patient-wearable sensor apparatus 100 may be configured with location tracking capability 110 which may include one or more of: GPS, or Wifi-based location tracking support. In some embodiments, patient-wearable sensor apparatus 100 may be configured to transmit or receive on any of communication links 108 aheartbeat, or beacon signal, which may be periodically sent and which signal may comprise modulated data including patient data, authentication data, or alert data.

The mobile event reporting system 300 illustrated in FIG. 3, of embodiments of the present invention includes: a smart-phone 301, communicatively coupled with both the patient-wearable sensor apparatus 100 of embodiments of the present invention and medication hub 200 in accordance with embodiments of the present invention.

The mobile event reporting system 300 of embodiments of the present invention is equipped with location tracking capability 302 which may include one or more of GPS or Wifi-based location tracking support, which may in some embodiments be provided by a smart-phone 301, and in other embodiments may be provided in the wearable sensor apparatus 100; in addition the smart-phone 301 of the mobile event reporting system of embodiments of the present invention is configured with: one or more application software 303 for communication of event, sensor, location, or alert data; and, wireless communications links 304, including one or more of Wifi, Zigbee, ANT, ANT+, Bluetooth, Broadband wireless, cellular communication, or other communication links known to one of ordinary skill in the art.

In some embodiments, smart-phone 301 may be configured with one or more machine learning or artificial intelligence algorithm 305 and associated data 306, where said associated data 306 may include training data, test data, validation data, historical data, alert thresholds, fall prediction thresholds, or profile data, and said one or more machine learning or artificial intelligence algorithm 305 may include: a neural network, a support vector machine, a decision tree, a classification tree, a regression tree, a random forest, a Bayes classifier, a genetic algorithm, or any other machine learning or artificial intelligence algorithm known to one of ordinary skill in the art.

In some embodiments, any element of patient-wearable sensor apparatus 100, medication hub 200, and mobile event reporting system 300 may be configured to transmit, receive, or respond to, with a similar response signal including information identifying the responding entity, on any communication link, a heartbeat, or beacon signal, which may be periodically sent and which signal may comprise modulated data including patient data, location data, event data, authentication data, or alert data.

In some embodiments, patient-wearable sensor apparatus 100, medication hub 200, and mobile event reporting system 300, may be configured to send, receive, and process event indications of fall, near-fall, and other types of events.

The patient-wearable sensor apparatus 100 of embodiments of the present invention may be embedded in an armband, wristband, chest strap, or other patient-wearable device. In the preferred embodiment of the present invention, the patient-wearable sensor apparatus 100 is positioned at the patient's chest for optimal fall detection and prediction using data from kinematic sensors 101 from the patient-wearable sensor apparatus 100; from a position at the patient's chest, kinematic sensor 101 data is representative of the motion of the patient's body core in addition to minimizing the effect on sensor data of extraneous extremity (e.g. arm or wrist) motion not related to a fall or near-fall. In further embodiments, patient-wearable sensor apparatus 100 may be embedded in the medication adherence support device disclosed in U.S. Provisional Patent Application Ser. No. 62120784, Medication Adherence Systems and Methods, filed Feb. 25, 2015, and attached to the patient's arm or wrist; in such scenarios, fall detection and prediction may be degraded in accuracy due to sensor data not representative of the motion of the patient's body core in addition to sensor data including extraneous extremity (e.g. arm or wrist) motion not related to a fall or near-fall, however techniques known to those of ordinary skill in the fields of signal processing, system identification, state estimation, spectral analysis, and filtering, such as Kalman or Complementary filtering, may be used to mitigate the accuracy degradation in fall detection and fall prediction by actively filtering or canceling extraneous extremity motion from the kinematic sensor 101 data used for fall detection and fall prediction. The kinematic sensor data of the patient-wearable sensor apparatus 100 of embodiments of the present invention provide a real-time indication of the angular momentum, altitude, and acceleration of the patient, in addition to the planetary magnetic field strength and direction experienced by the patient.

The one or more machine learning or artificial intelligence algorithm 106 or 220 processes the sensor data to discriminate between falls and non-falls, for the purpose of reducing false positives for non-fall or near-fall events, and reducing false negatives for real fall events. The patient-wearable sensor apparatus 100 communicates the kinematic sensor data to medication hub 200 and smart-phone 301 of the mobile event reporting system 300 in accordance with embodiments of the present invention.

In an exemplary embodiment of the present invention, the machine learning or artificial intelligence algorithm 106 processing the kinematic sensor 101 data for fall detection is configured to operate in the patient-wearable sensorapparatus 100. In further embodiments, the machine learning or artificial intelligence algorithm 220 processing the kinematic sensor 101 data for fall detection may be configured to operate in the medication hub 200 in accordance with embodiments of the present invention; in still further embodiments, the smart-phone 301 application software 303 may also be configured to operate the machine learning or artificial intelligence algorithm 305 processing the sensor data for fall detection discrimination; in additional embodiments, the machine learning or artificial intelligence algorithm processing the sensor data for fall detection discrimination may be collaboratively operated in all of the patient-wearable sensor apparatus 100, the medication hub 200 in accordance with embodiments of the present invention, and the smart-phone 301 in accordance with embodiments of the present invention.

In scenarios where the patient is indoors or otherwise within communication range of the medication hub 200 in accordance with embodiments of the present invention, the medication hub 200 or patient-wearable sensor apparatus 100, or both, receive and process the kinematic sensor data to detect falls in addition to screening potential fall events by further processing the sensor data with one or more machine learning or artificial intelligence algorithm 106 or 220; when a fall or near-fall event is classified by either the patient wearable sensor apparatus 100 or medication hub 200, as a real fall or near-fall, if processing of sensor data was performed on the patient-wearable sensor apparatus 100, the medication hub 200 will be notified of the event by the patient-wearable sensor apparatus 100, and the medication hub 200 may initiate actions as configured including: sending alerts to caregivers, auditing, adjusting alert thresholds, adjusting profile data representative of patient activity, or recalculating fall prediction thresholds; when a fall event is classified as a real fall, the medication hub will initiate actions as configured including sending alerts to caregivers, including the patient's current location in the home as configured or detected in the medication hub 200.

In scenarios where the patient is outdoors or otherwise not within communication range of the medication hub 200, the patient-wearable sensor apparatus 100 receives and processes the sensor data to detect falls in addition to screening potential fall events by further processing the kinematic sensor 101 data with one or more machine learning or artificial intelligence algorithm 106; when a fall or near-fall event is classified, as a real fall or near-fall, patient-wearable sensor apparatus 100 will direct the smart-phone 301 application software 303 of the mobile event reporting system 300 to initiate actions as configured including: sending alerts to caregivers, communicating with the medication hub 200 via the internet using wifi or Broadband wireless to include auditing, adjusting alert thresholds, adjusting profile data representative of patient activity, or recalculating fall prediction thresholds; when a fall event is classified as a real fall, the patient-wearable sensor apparatus 100 will notify the smart phone 301 application software 303 to initiate actions as configured, including sending alerts to caregivers, which alerts may include text messages, with the coordinates of the patient's current location as reported by the smart-phone 301 location tracking capability 302.

If caregivers have alerted first responders to locate the patient, the smart-phone 301 application software 303 of the mobile event reporting system 300 of embodiments of the present invention may switch the smart-phone 301 wifi subsystem to ad-hoc mode, and transmit an SSID identifying the patient by account or subscriber id, or the SSID may be configured on a per-incident basis, to help responders find the patient by using wifi scanners and signal strength monitors, where a stronger signal indicates closer proximity to the patient's smart-phone 301.

The one or more of a machine learning or artificial intelligence algorithm 106 or 220 may be configured with a generic training that approximates a fall detection, before delivery to a particular patient, and subsequent to delivery, training may be optimized for the individual user by capturing baseline training data for a user and performing additional training steps; for example, individual users may have varying motion profiles when sitting down, and training beyond the initially-provided generic training may be beneficial to discriminate between a real fall event and the user's normal sitting-down movement and impact to a chair.

Kinematic sensor 101 data at the patient-wearable sensor apparatus 100 may in general be used with timing and historical data to detect falls as follows: Altimeter 103 data representative of patient altitude can be used to detect a sudden drop to an altitude representative of the ground level, in combination with sudden deceleration data from the accelerometer 102 data representative of patient acceleration, which may indicate impact with a hard surface; in addition, magnetometer 105 data representative of patient orientation can indicate a sudden, approximately ninety-degree shift in the direction of the planetary magnetic field. In addition, gyroscope 104 data representative of patient angular momentum from the patient-worn sensor may indicate a sudden twisting motion as a patient loses their footing, which may be followed in a real fall event by the previously described indications of a fall as measured by altimeter 103, accelerometer 102, and magnetometer 105 data.

In further embodiments, the patient-wearable sensor apparatus 100 may include a microphone 111 and associated Internet Protocol (IP) Telephony supporting software, to allow a patient to speak to caregivers, having their voice relayed to caregivers through any available communication link 108, including through any communication capability or resource available to the medication hub 200 or smart-phone 301.

In further embodiments, the patient-wearable sensor apparatus 100 or smart-phone 30 application software 303 may include a low battery alarm warning system. GPS and location-aware services frequently present severe battery power drain in mobile devices, resulting in limited operating time, which may leave a patient at risk of losing the benefit of fall detection monitoring if battery power level is already low when a patient begins even a short journey from their home. The low battery alarm warning system of embodiments of the present invention serves to detect when the battery level in any of the smart-phone 301 or the patient-wearable sensor apparatus may be too low for sustained location-aware (i.e. with GPS coordinates of patient location) fall detection, fall prevention, and alerting. If battery levels are too low to permit sustained fall detection (i.e. below a configurable threshold of time remaining or other indication of battery power level) an immediate alert may be sent, with the patient's location and direction, in accordance with embodiments of the present invention, to caregivers, even when a fall or near-fall event has not occurred, in addition to warning the patient that battery levels are low and they should return home and recharge.

In some embodiments, the application software 303 of smart-phone 301, medication hub 200, or patient-wearable sensor apparatus 100, may track patients distance and estimated time to return to a charging station, and issue a low-battery alert to a patient and caregivers when, due to distance from home, battery energy level may be insufficient to provide continuous fall detection without further battery charging. In some embodiments, in a low battery scenario, alerts with the patient location may continue to be sent while battery power remains, to provide the most recent location; in further embodiments, GPS and wireless broadband interfaces in the smart-phone 301 may be powered down temporarily, and periodically re-powered to obtain and send patient location data to caregivers on less frequent intervals to conserve power, as configured.

In some embodiments, if the patient-wearable sensor apparatus 100 fails due to low battery or other causes, and only the smart-phone 301 is available to the patient, the smart-phone 301 application software 303 may fall back to using one or more of the smart-phone 301 accelerometer or magnetometer for fall detection, if available in the smart-phone 301 as is common in the art of mobile devices including smart phones, sending an alert indicating reduced system capability, while continuing to send alerts of fall events with location data as disclosed herein.

In some embodiments, mobile event reporting system 300 may equip smart-phone 301 with an externally connected dongle device 307 configured with kinematic sensors as disclosed herein for the patient-wearable sensor apparatus 100, to enable smart-phone 301 to function as a backup fall-detection device with improved kinematic sensors when compared to the typical sensor quality of commonly available smart-phones.

In still further embodiments, the patient-wearable sensor apparatus 100 may include a heart rate sensor 112, taking advantage of the preferred positioning of the patient-wearable sensor apparatus 100 at the chest for optimal fall detection, to also sense, record, report, and analyze the patient's heart function.

In addition to fall detection, embodiments of the present invention provide fall prevention through automated and continuous fall prediction integrated with the medication adherence of embodiments of the invention disclosed in U.S. Provisional Patent Application Ser. No. 62120784, Medication Adherence Systems and Methods, filed Feb. 25, 2015.

Embodiments of the present invention may continuously capture and analyze with respect to time kinematic sensor data representative of patient acceleration, orientation, angular momentum, and altitude, detecting patient activity events such as standing up, sitting down, uninterrupted walking (e.g. walking through a hallway), and similar events related to patient activities of daily living (ADL).

Embodiments of the present invention may analyze data from kinematic sensor 101 captured before, during, and after an event representative of patient ADL, and compare data and analysis from an ADL event happening in the present to data and analysis from one or more of a similar past ADL event.

The data from kinematic sensor 101 may be used by embodiments of the present invention to automate portions of standardized fall prediction assessments commonly used in clinical settings for decades; in a non-limiting example, clinical balance and motor assessments that can be automated include: portions of the Berg Balance Assessment, the Tinetti Test, the Timed Up and Go Test, and other similar tests.

Furthermore, the data and analysis in many cases can be captured and analyzed without interrupting the patient's daily activity or schedule. For example, each time the patient sits down or stands up at medication hub 200, for example, as part of a regular medication dosing schedule, data from kinematic sensor 101 captured before, during, and after the patient sits down or stands up may be captured, analyzed, and compared with baseline data which may comprise averages or other statistical analyses of kinematic sensor 101 data from past events of the same patient sitting down or standing up. Analysis of trials of data from kinematic sensor 101 may include statistical processing, goodness of fit tests, signal processing, spectral analysis, filtering, or other techniques for anomaly detection, signal classification, kinematic event detection, or signal identification, as are known to those of ordinary skill in the art.

When anomalies are detected in the patient's balance or stability in data from kinematic sensor 101 as compared with baseline data for the patient or a population of patients, supervised testing of the patient with subsequent capture of data from kinematic sensor 101 further analysis may be performed interactively with caregivers via video or audio links in medication hub 200.

Further standardized balance assessments that may be automated by embodiments of the present invention include, in a non-limiting example, detecting when a patient stands up, and continuously capturing and analyzing data from kinematic sensor 101 to assess the patient's balance and stability on their feet in the first five seconds (or other configured period of time) after standing; this replicates a commonly used clinical balance assessment; embodiments of the present invention may perform this or similar kinematic sensor data capture and analysis, storing the analysis and data for reference comparison, and use past and present data representative of patient stability and balance after standing to assess the impact of the patient's condition and treatment on the patient's balance, alerting caregivers or otherwise intervening in the patient's treatment if balance or stability has degraded and if the degradation in balance or stability can be correlated with a change in the patient's health or treatment regimen.

The Timed Up and Go Test, and other similar standardized assessments, may also be automated in a supervised setting, via video or audio link with caregivers, through medication hub 200.

The standardized balance and mobility assessments mentioned herein are exemplary and non-limiting, and many other balance or mobility assessments for fall prediction may be automated by embodiments of the present invention, through the detection of patient ADL events, comparison and analysis of captured baseline and test data during dosing, including standing up and sitting down, assessing balance in the first five seconds after standing, and analyzing and assessing the patient's gait.

When anomalies in patient daily performance from degraded balance and mobility are detected by medication hub 200 using data from kinematic sensor 101, falls may be more likely, and medication hub 200 may alert caregivers, advise the patient to remain in the home, adjust fall detection thresholds, or adjust dosing regimen, or take other actions as appropriate and as configured.

The data captured from kinematic sensor 101 is analyzed by embodiments of the present invention to aid in fall prevention through fall prediction integrated with medication adherence through medication hub 200.

Standardized fall prediction analysis based on balance and mobility assessments in accordance with well-known clinical tests is implemented in embodiments of the present invention in medication hub 200 and patient-wearable sensor apparatus 100, and these results are compared with baseline data for the patient to determine if the patient's balance or stability has changed.

In some embodiments, if a patient's balance or stability has changed, medication hub 200 may be configured to review recent dosing changes, medication changes, medication adherence audit results, or dose compliance audit results, alerting caregivers if a potential drug interaction, recent dosing anomaly, or recent dosing change, may have contributed to the patient's loss of balance.

Embodiments of the present invention integrate medication adherence and treatment with fall detection and fall prediction to provide fall prevention by continuously monitoring patient motion and detecting with machine learning and artificial intelligence when patient motion is less stable or more erratic than normal for that patient, and may predict that falling is more likely and advise the patient to be more cautious, or alert caregivers that intervention may be beneficial, or may trigger adjustment to medication dosing or automatic review of medication adherence audit records in accordance with embodiments of the invention disclosed in U.S. Provisional Patent Application Ser. No. 62120784, Medication Adherence Systems and Methods, filed Feb. 25, 2015.

In addition to kinematic sensor 101 data, in some embodiments patient heart activity data from heart rate sensor 112 may be used to monitor for anomalous heart rate activity and alerts may be issued or interventions may be engaged if patient heart rate anomalies are detected.

In further embodiments, anomalous heart rate activity detected by analysis and classification of data from heart rate sensor 112 may trigger adjustment to medication dosing or automatic review of medication adherence audit records in accordance with embodiments of the invention disclosed in U.S. Provisional Patent Application Ser. No. 62120784, Medication Adherence Systems and Methods, filed Feb. 25, 2015.

Figure 4:
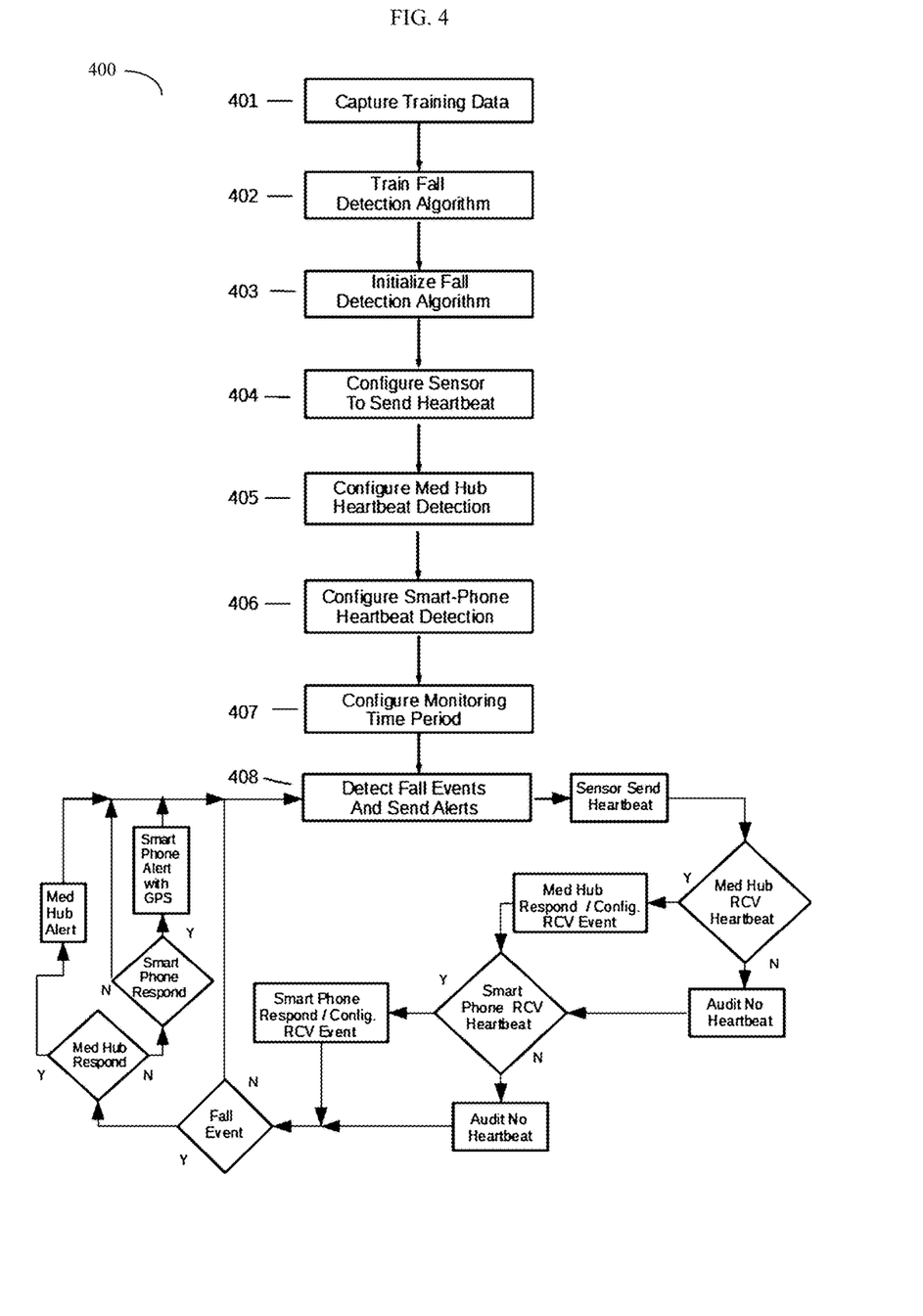
FIG. 4 illustrates a process flow for automatic fall detection, in accordance with an embodiment of the present invention.

Referring now to FIG. 4, in accordance with some embodiments of the present invention, a process flow 400 for automatic fall detection is disclosed. In a first stage, at step 401, patient-wearable sensor apparatus 100 is configured to continuously capture, sample, filter, and analyze baseline kinematic fall detection data representative of: patient Activities of Daily Living, fall events, and near-fall events, from kinematic sensor 101, including data representative of patient acceleration, orientation, angular momentum, and altitude. In a second stage, at step 402, one or more of machine learning or artificial intelligence algorithm 106 is trained on said baseline kinematic fall detection data to discriminate between patient Activities of Daily Living, fall events, and near-fall events, and the trained configuration is stored. In a third stage, at step 403, one or more of machine learning or artificial intelligence algorithm 106 in patient-wearable sensor apparatus 100 is initialized with a trained configuration resulting from the second stage. In a fourth stage, at step 404, patient wearable sensor apparatus 100 is configured to transmit a heartbeat signal detectable by either medication hub 200 or smart-phone 301. In a fifth stage, at step 405, medication hub 200 is configured to detect a heartbeat signal sent by patient-wearable sensor apparatus 100. In a sixth stage, at step 406, smart-phone 301 is configured to detect a heartbeat signal sent by patient-wearable sensor apparatus 100.

In a seventh stage, at step 407, a fall-detection monitoring time period is configured in patient-wearable sensor apparatus 100, medication hub 200, and smart-phone 301.

In an eighth stage, at step 408, for each fall-detection monitoring time period in a countably infinite set of one or more sequential fall-detection monitoring time period, detect fall events and send alerts, comprising the steps of: sending a heartbeat signal from patient-wearable sensor apparatus 100; performing a test at medication hub 200 to determine if heartbeat signal from patient-wearable sensor apparatus 100 is detected by medication hub 200; upon a determination that heartbeat signal from patient-wearable sensor apparatus 100 is detected by medication hub 200, medication hub 200 sends a response with information identifying medication hub 200 and medication hub 200 is configured to receive one or more event indication; upon a determination that heartbeat signal from patient-wearable sensor apparatus 100 is not detected by medication hub 200, medication hub 200 audits no heartbeat detected; performing a test at smart-phone 301 to determine if heartbeat signal from patient-wearable sensor apparatus 100 is detected by smart-phone 301; upon a determination that heartbeat signal from patient-wearable sensor apparatus 100 is detected by smart-phone 301, smart-phone 301 sends a response with information identifying smart-phone 301 and smart-phone 301 is configured to receive one or more event indication; upon a determination that heartbeat signal from patient-wearable sensor apparatus 100 is not detected by smart-phone 301, smart-phone 301 audits no heartbeat detected; patient-wearable sensor apparatus 100 is configured to continuously, for at least a fall-detection monitoring time period, capture, sample, filter, and analyze kinematic test data from kinematic sensor 101, including data representative of patient acceleration, orientation, angular momentum, and altitude; present as input said kinematic test data from kinematic sensor 101 to one or more of machine learning or artificial intelligence algorithm 106 in patient-wearable sensor apparatus 100; monitor output of one or more of machine learning or artificial intelligence algorithm 106 in patient-wearable sensor apparatus 100 to determine if a fall or near-fall event was detected in patient-wearable sensor apparatus 100; upon a determination that a fall or near-fall event was not detected in patient-wearable sensor apparatus 100, audit no fall event at patient-wearable sensor apparatus 100; upon a determination that a fall or near-fall event was detected at patient-wearable sensor apparatus 100: a test is performed at patient-wearable sensor apparatus 100 to determine if a heartbeat response was received at patient-wearable sensor apparatus 100 from medication hub 200; upon a determination that a heartbeat response was received from medication hub 200 at patient-wearable sensor apparatus 100, patient-wearable sensor apparatus 100 sends a fall event to medication hub 200; upon a determination that no heartbeat response was received from medication hub 200 at patient-wearable sensor apparatus 100, patient-wearable sensor apparatus 100 audits no heartbeat response received from medication hub 200; a test is performed at patient-wearable sensor apparatus 100 to determine if a heartbeat response was received at patient-wearable sensor apparatus 100 from smart-phone 301; upon a determination that a heartbeat response was received from smart-phone 301 at patient-wearable sensor apparatus 100, patient-wearable sensor apparatus 100 sends fall event to smart-phone 301; upon a determination that no heartbeat response was received from smart-phone 301 at patient-wearable sensor apparatus 100, patient-wearable sensor apparatus 100 audits no heartbeat response received from smart-phone 301; a test is performed at medication hub 200 to determine if a fall event was received from patient-wearable sensor apparatus 100 at medication hub 200; upon a determination a fall event was received from patient-wearable sensor apparatus 100 at medication hub 200, medication hub 200 sends an alert to caregivers indicating medication hub 200 as the source of the alert; upon a determination a fall event was not received from patient-wearable sensor apparatus 100 at medication hub 200, medication hub 200, medication hub audits no fall event at medication hub 200; a test is performed at smart-phone 301 to determine if a fall event was received from patient-wearable sensor apparatus 100 at smart-phone 301; upon a determination a fall event was received from patient-wearable sensor apparatus 100 at smart-phone 301, smart-phone 301 sends an alert to caregivers with GPS coordinates from smart-phone 301 indicating smart-phone 301 as the source of the alert; upon a determination a fall event was not received from patient-wearable sensor apparatus 100 at smart-phone 301, smart-phone 301, smart-phone 301 audits no fall event at smart-phone 301.

Figure 5:
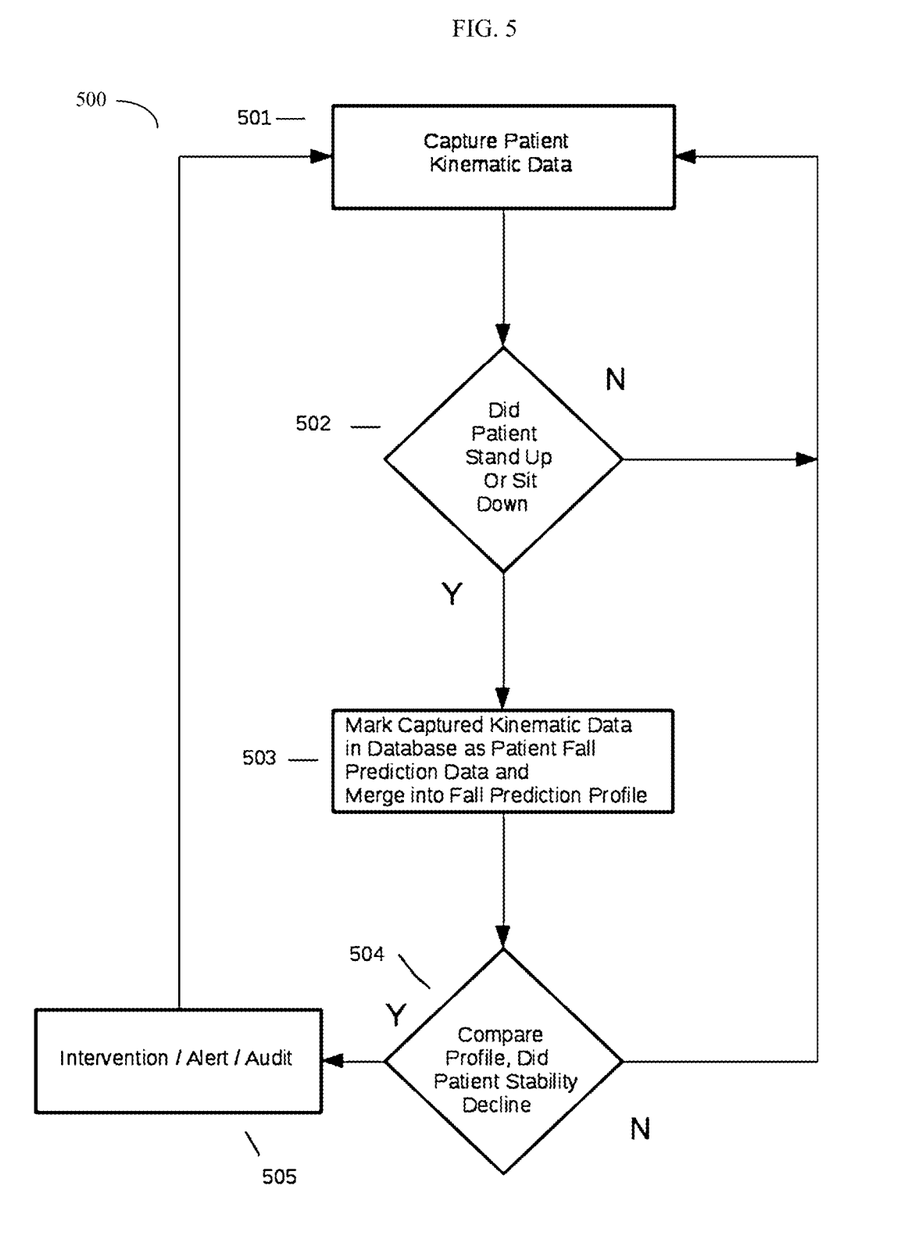
FIG. 5 illustrates a process flow for fall prevention, in accordance with an embodiment of the present invention.

Referring now to FIG. 5, in accordance with some embodiments of the present invention, a process flow 500 for fall prediction is disclosed. In a first stage, at step 501, kinematic data representative of patient motion is continuously captured from patient-wearable kinematic sensor apparatus 100, said kinematic data including patient altitude, patient acceleration, patient orientation, and patient angular momentum.

In a second stage, at step 502, a test is performed at kinematic sensor apparatus 100 to determine when and if patient sat down before medication dosing or stood up after medication dosing at medication hub 200 for medication adherence protocols.

In a third stage, at step 503, upon a determination patient sat down before or stood up after medication dosing at medication hub 200 for medication adherence protocols, captured kinematic data from kinematic sensor apparatus 100 is marked in one or more database as comprising fall-prediction data, and the patient's currently captured fall-prediction data is merged into the patient's historical fall-prediction profile comprising all previously captured fall-prediction data for the same patient.

Upon a determination patient did not sit down before or stand up after medication dosing at medication hub 200 for medication adherence protocols, processing continues at step 501, with kinematic data representative of patient motion continuously captured from patient-wearable kinematic sensor apparatus 100.

In a fourth stage, at step 504, the patient's currently captured fall-prediction data is compared to historical fall-prediction profile for the same patient, and a test is performed using currently-captured patient angular momentum and patient acceleration data and the patient's historical fall-prediction profile, to determine if the patient's balance and stability have degraded relative to patient's historical fall-prediction profile.

In a fifth stage, at step 505, upon a determination the patient's balance and stability has degraded relative to patient's historical fall-prediction profile, embodiments of the present invention may intervene in patient care in multiple ways including: alerting caregivers that falls may be more likely due to decreased patient stability; adjusting fall detection thresholds or re-configuring fall detection models to be more sensitive in alerting caregivers to near-fall events; or, correlating decreased balance with medication adherence auditing at medication hub 200, including: reviewing recent medication dosing changes, identifying and resolving potential drug interaction, and confirming medication dose adherence; upon a determination the patient's balance and stability has not degraded relative to patient's historical fall-prediction profile, processing continues at step 501, with kinematic data representative of patient motion continuously captured from patient-wearable kinematic sensor apparatus 100.

The following claims are provided to add additional clarity to this disclosure. Future applications claiming priority to this application may or may not include the following claims, and may include claims broader, narrower, or entirely different from the following claims.

The invention claimed is:

1. A method for automatic fall detection, comprising the steps of:
    configuring a patient-wearable kinematic sensor to continuously capture, sample, filter, and analyze baseline kinematic fall detection data representative of: patient Activities of Daily Living, fall events, and near-fall events, from said patient wearable kinematic sensor, including data representative of patient acceleration, patient orientation, patient angular momentum, and patient altitude;
    training one or more machine learning or artificial intelligence algorithm on said baseline kinematic fall detection data to discriminate between patient Activities of Daily Living, patient fall events, and patient near-fall events, and storing the trained configuration;
    initializing one or more machine learning or artificial intelligence algorithm in said patient-wearable kinematic sensor with said trained configuration;
    configuring said patient-wearable kinematic sensor to transmit a heartbeat signal detectable by either or both of a medication hub or smart-phone;
    configuring said medication hub to receive and detect a heartbeat signal sent by said patient-wearable kinematic sensor;
    configuring said smart-phone to receive and detect a heartbeat signal sent by said patient-wearable kinematic sensor;
    configuring a fall-detection monitoring time period in said patient-wearable kinematic sensor, said medication hub, and said smart-phone; and, for each fall-detection monitoring time period in a countably infinite set of one or more sequential fall-detection monitoring time period, detecting patient fall events and sending alerts, wherein for each said fall-detection monitoring time period in a countably infinite set of one or more sequential fall-detection monitoring time period, detecting patient fall events and sending alerts includes:
    transmitting a heartbeat signal from said patient-wearable kinematic sensor;
    performing a test at said medication hub to determine if said heartbeat signal from patient-wearable kinematic sensor is detected by said medication hub;
    upon a determination said heartbeat signal from said patient-wearable kinematic sensor is detected by said medication hub, sending from said medication hub a response with information identifying said medication hub and configuring said medication hub to receive one or more event indication;
    upon a determination said heartbeat signal from said patient-wearable kinematic sensor is not detected by said medication hub, auditing at said medication hub no heartbeat detected; performing a test at said smart-phone to determine if said heartbeat signal from said patient-wearable kinematic sensor is detected by said smart-phone;
    upon a determination said heartbeat signal from said patient-wearable sensor is detected by said smart-phone, sending from said smart-phone a response with information identifying said smart-phone and configuring said smart-phone to receive one or more event indication;
    upon a determination said heartbeat signal from said patient-wearable sensor is not detected by said smart-phone, auditing at said smart-phone no heartbeat detected;
    configuring said patient-wearable kinematic sensor to continuously, for at least a fall-detection monitoring time period, capture, sample, filter, and analyze kinematic test data, including data representative of patient acceleration, patient orientation, patient angular momentum, and patient altitude;
    presenting as input said kinematic test data to said one or more machine learning or artificial intelligence algorithm in said patient-wearable kinematic sensor;
    monitoring, in said patient-wearable kinematic sensor, one or more output of said one or more machine learning or artificial intelligence algorithm and performing a test in said patient-wearable kinematic sensor of said one or more output of said one or more machine learning or artificial intelligence algorithm to determine if a fall or near-fall event is detected;

upon a determination that a fall or near-fall event is not detected in said patient-wearable kinematic sensor, auditing at said patient-wearable kinematic sensor no fall event;

upon a determination that a fall or near-fall event is detected at said patient-wearable kinematic sensor, performing a test at said patient-wearable kinematic sensor to determine if said heartbeat response was received at said patient-wearable kinematic sensor from said medication hub;

upon a determination that said heartbeat response was received from said medication hub at said patient-wearable kinematic sensor, sending from said patient-wearable kinematic sensor a fall event to said medication hub;

upon a determination that no said heartbeat response was received from said medication hub at said patient-wearable sensor, auditing at said patient-wearable kinematic sensor no said heartbeat response received from said medication hub;

performing a test at said patient-wearable kinematic sensor to determine if said heartbeat response was received at said patient-wearable kinematic sensor from said smart-phone;

upon a determination that said heartbeat response was received from said smart-phone at said patient-wearable kinematic sensor, sending from said patient-wearable kinematic sensor a fall event to said smart-phone;

upon a determination that no said heartbeat response was received from said smart-phone at said patient-wearable kinematic sensor, auditing at said patient-wearable kinematic sensor no said heartbeat response received from said smart-phone;

performing a test at said medication hub to determine if a fall event was received from said patient-wearable kinematic sensor at said medication hub;

upon a determination a fall event was received from said patient-wearable kinematic sensor at said medication hub, sending from said medication hub an alert to caregivers indicating said medication hub as the source of the alert;

upon a determination a fall event was not received from said patient-wearable kinematic sensor at said medication hub, auditing at said medication hub no fall event;

performing a test at said smart-phone to determine if a fall event was received from said patient-wearable kinematic sensor at said smart-phone;

upon a determination a fall event was received from said patient-wearable kinematic sensor at said smart-phone, sending from said smart-phone an alert to caregivers indicating said smart-phone as the source of the alert, said alert including GPS coordinates from said smart-phone; and upon a determination a fall event was not received from patient-wearable kinematic sensor apparatus at said smart-phone, auditing at said smart-phone no fall event.

\* \* \* \* \*